United States Patent
Battefeld et al.

(10) Patent No.: US 8,069,706 B2
(45) Date of Patent: Dec. 6, 2011

(54) WASTE WATER IMMERSION PROBE

(75) Inventors: Manfred Battefeld, Dusseldorf (DE); Andreas Jonak, Meerbusch (DE); Lothar Heidemanns, Korschenbroich (DE); Axel Leyer, Monchengladbach (DE); Michael Schuster, Neuss (DE)

(73) Assignee: Hach Lange GmbH, Berlin (DE)

( * ) Notice: Subject to any disclaimer, the term of this patent is extended or adjusted under 35 U.S.C. 154(b) by 581 days.

(21) Appl. No.: 12/278,480

(22) PCT Filed: Jan. 16, 2007

(86) PCT No.: PCT/EP2007/050417
§ 371 (c)(1),
(2), (4) Date: Nov. 4, 2008

(87) PCT Pub. No.: WO2007/090717
PCT Pub. Date: Aug. 16, 2007

(65) Prior Publication Data
US 2009/0301175 A1    Dec. 10, 2009

(30) Foreign Application Priority Data
Feb. 6, 2006   (EP) .................................... 06101329

(51) Int. Cl.
*G01N 29/00* (2006.01)
*G01N 33/18* (2006.01)

(52) U.S. Cl. ..................... 73/53.01; 73/61.48; 73/61.49; 73/61.71; 73/61.79; 73/64.53; 15/250.001; 15/250.31; 15/250.34

(58) Field of Classification Search .................. 73/53.01, 73/61.48, 61.49, 61.71, 61.79, 64.53, 64.56; 15/246, 250.001, 250.31, 250.34
See application file for complete search history.

(56) References Cited

U.S. PATENT DOCUMENTS

| | | | |
|---|---|---|---|
| 3,844,661 A * | 10/1974 | Birkett et al. ................. | 356/414 |
| 4,818,132 A * | 4/1989 | Brull et al. ..................... | 400/708 |
| 4,896,047 A * | 1/1990 | Weaver et al. ................ | 250/573 |

(Continued)

FOREIGN PATENT DOCUMENTS
DE         33 29 215 A1    2/1985
(Continued)

OTHER PUBLICATIONS

International Search Report issued in related application No. PCT/EP2007/050415, completed Mar. 29, 2007 and mailed Apr. 11, 2007.

(Continued)

*Primary Examiner* — Daniel Larkin
(74) *Attorney, Agent, or Firm* — Norman B. Thot

(57) ABSTRACT

The invention relates to a waste water immersion probe (10) comprising a liquid-tight housing (11), a sensor (18) which is disposed in the housing (11) and a sensor window (20) formed on the housing (11). A wiper element (22) for cleaning the sensor window (20) is arranged on the outside of the sensor window (20), and the wiper element (22) is driven by a drive motor (24) which is arranged essentially in the housing (11). The housing is devoid of openings. A magnetic element (36, 37) is associated with the drive motor (24) and a magnetic element (34, 35) is associated with the wiper element (22) in such a manner that the magnetic drive motor element (36, 37) produces a magnetic field which transverses the housing wall and transmits a drive torque to the wiper element (22) without a shaft.

16 Claims, 1 Drawing Sheet

U.S. PATENT DOCUMENTS

| | | | |
|---|---|---|---|
| 5,072,615 A | | 12/1991 | Nawrocki |
| 5,479,077 A | * | 12/1995 | Kline et al. ............... 318/443 |
| 6,779,383 B2 | * | 8/2004 | Lizotte et al. ............. 73/61.48 |
| 6,938,506 B2 | * | 9/2005 | Henry et al. .............. 73/866.5 |
| 7,634,937 B2 | * | 12/2009 | Burdett et al. ............. 73/24.06 |
| 2005/0207939 A1 | * | 9/2005 | Roussi et al. ............. 422/68.1 |

FOREIGN PATENT DOCUMENTS

| | | | |
|---|---|---|---|
| DE | 3936753 A1 | * | 5/1991 |
| DE | 42 33 218 A1 | | 4/1994 |
| EP | 0 437 872 A2 | | 7/1991 |
| EP | 0 590 487 A1 | | 4/1994 |
| EP | 0 634 645 A1 | | 1/1995 |
| EP | 0 901 020 A2 | | 3/1999 |
| JP | 55-107910 | * | 8/1980 |
| JP | 5-159339 | * | 6/1993 |

OTHER PUBLICATIONS

International Search Report issued in corresponding application No. PCT/EP2007/050417, completed Mar. 12, 2007 and mailed Mar. 19, 2007.

English translation of International Preliminary Report on Patentability issued in corresponding application No. PCT/EP2007/050417.

Anonymus: Firmenprospekt "Process-Messtechnik" der Firma Hach Lange GmbH, Teil 4, Jan. 4, 2004, pp. 83-133, XP002382972.

* cited by examiner

WASTE WATER IMMERSION PROBE

This is a National Phase Application in the United States of Application No. PCT/EP2007/050417 filed Jan. 16, 2007, which claims priority on European Patent Application No. 06101329.8, filed Feb. 6, 2006. The entire disclosures of the above patent applications are hereby incorporated by reference.

TECHNICAL FIELD

The invention is directed to a waste water immersion probe comprising a liquid-tight housing with a sensor window and a wiper for cleaning the sensor window on the outer side.

BACKGROUND OF THE INVENTION

Waste water immersion probes are used for the detection of various parameters in waste water. Examples of these probes are turbidity sensors or solid matter sensors, ultrasonic sludge blanket probes, UV or nitrate probe, etc. In each of these immersion probes, a sensor is arranged in the housing that, through a sensor window in or at the housing, measures one of the mentioned parameters in the waste water outside the housing. Accretions on the outside of the sensor window can corrupt or even make the sensor measurements impossible.

From DE 4 233 218 A1, a waste water immersion probe for turbidity measurement is known. The sensor is an optical sensor that receives light through an optical window. The sensor window can be cleaned by a wiper sweeping across the outer side of the sensor window. The wiper is driven by an electric drive motor arranged in the housing. The drive motor and the wiper are connected via a shaft passing through an opening in the housing. Thus, the shaft has to be sealed by means of a shaft sealing. Experience has shown that shaft sealings only have a limited sealing effect or seal reliably only for a limited time. In the event of a leak, liquid enters the housing so that the housing is eventually flooded and the components therein are destroyed.

BRIEF SUMMARY OF THE INVENTION

In view of this, it is an object of the invention to provide a waste water immersion probe with improved sealing.

The waste water immersion probe of the present invention has a housing devoid of openings, i.e. it has at least no opening for a drive shaft. Both the drive motor and the wiper are associated with a respective magnetic element by which the drive motor is coupled with for the transmission of torques. The magnetic element of the drive motor generates a magnetic field permeating the non-metallic housing wall, which magnetic field is adapted to move or take along the magnetic element of the wiper. Of course, a cinematic inversion is also possible, i.e. the magnetic element of the wiper generates a magnetic field by which the wiper is coupled, with respect to force, with the respective magnetic element of the drive motor. As an alternative, both the elements of the wiper and the drive motor can be magnetized as well, i.e. generate a magnetic field.

A contactless and shaft-free mechanical coupling of the drive motor with the wiper is thus realized, making a housing opening for a drive shaft dispensable. By the omission of the housing opening for the drive shaft, the main reason for the entry of humidity or liquid from the waste water into the housing is obviated. This significantly increases the reliability and the average service life of the waste water immersion probe. The magnetic coupling of the drive motor with the wiper further forms a slipping clutch that limits the torque transmittable. This provides a better protection of the wiper against deformation and damage in the event of collisions.

A passive magnetic coupling of the drive motor element with the wiper element can basically be realized in two different ways. On the one hand, the coupling can be effected through permanent magnets on both elements, however, the coupling may also be effected by permanent magnets on one element and ferromagnetic non-magnetized parts on the other element.

As an alternative, in an active magnetic variant, the housing-side element can be designed as a stator and the wiper-side element can be configured as a permanently excited rotor of an electric motor forming the drive motor.

While the passive magnetic coupling is structurally rather simple and can be mostly realized using standard components, the active magnetic variant of the drive motor/wiper coupling is a space saving solution with which even higher torques can be transmitted, if necessary.

In a preferred embodiment, the wiper movement is an oscillatory movement and stop elements are provided on the outside of the housing and the wiper, which stop elements mechanically limit the oscillating wiping movement. The stop elements reliably limit the wiping angle of the wiper. Since the magnetic coupling of the drive motor and the wiper is restricted to a maximum torque, the coupling may cause a "cycle error" due to the occurrence of a torque higher than the maximum, which may be due to soiling, the wiper getting stuck, or other external influences, so that the wiper subsequently no longer or only partly wipes the sensor window. The stop elements guarantee that the wiper returns to its initial position after a full wiping sequence and again sweeps the entire intended wiping area. The stop elements further prevent the out-of-step wiper from leaving the defined wiping area at all.

In a preferred embodiment, the wiper comprises an annular body containing the magnetic element or the magnetic elements, the annular body sitting on a housing-side pot or surrounds the same in a ring-like manner. When the magnetic drive motor and wiper elements are embodied as an electric motor, the pot forms a so-called split pot. The pot or the split pot is made of non-magnetic material.

Preferably, a spoiler is associated with the housing, which radially covers a circular gap opening between the annular body of the wiper and the housing. Generally, solid matter from the waste water, especially fibrous solid matter in passing waste water, may enter the gap opening and be caught there. The spoiler deflects this solid matter such that they do not get into the circumferential circular gap opening. Thus, an intrusion of especially fibrous solid matter into the gap opening and a resulting jamming of the wiper's annular body on the housing pot is avoided.

Preferably, a radial play is provided between the annular body of the wiper and the pot of the housing, the radial guiding of the annular body of the wiper being effected exclusively by a locking disc fastened centrally in the axial direction on the pot. The locking disc forms an annular contact line together with the annular body of the wiper. Thus, the radial bearing surface is limited to a very small area so that the bearing friction is also reduced to a minimum. This is of particular importance because the magnetic coupling of the wiper with the drive motor can transmit only a rather low torque.

In a preferred embodiment, the annular body of the wiper is biased axially by the magnetic elements of the wiper and the drive motor. Preferably, the annular body of the wiper is biased in the proximal direction, that is towards the housing.

In the distal direction, a certain play remains between the annular body of the wiper and the locking disc. Thereby, jamming can largely be excluded. The axial bias and a certain axial play of the annular body of the wiper together cause the wiper to be pressed against the sensor window with a defined force. Should the wiper meet a small obstacle, it may still tilt by overcoming the axial bias force and thereby evade the obstacle. The axial bias is chosen such that only rather low axial friction forces occur between the annular body of the wiper and the housing and that a reliable radial guiding of the annular body on the locking disc is effected.

In a preferred embodiment, the locking disc and the pot have catch elements by which the locking disc is caught in its locked position on the pot. This catching secures the locking disc against inadvertent loosening, such as by vibrations and the like, for example.

BRIEF DESCRIPTION OF THE DRAWINGS

The following is a detailed description of an embodiment of the invention with reference to the drawings.

In the Figures.

DETAILED DESCRIPTION OF THE INVENTION

Figure 1:
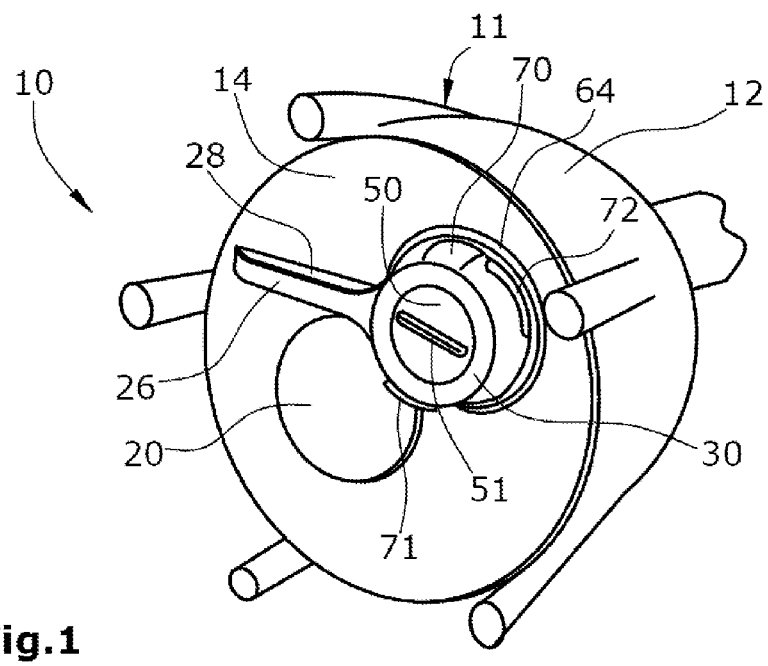
FIG. 1 is a perspective bottom view of a waste water immersion probe with a magnetically coupled wiper.
Figure 2:
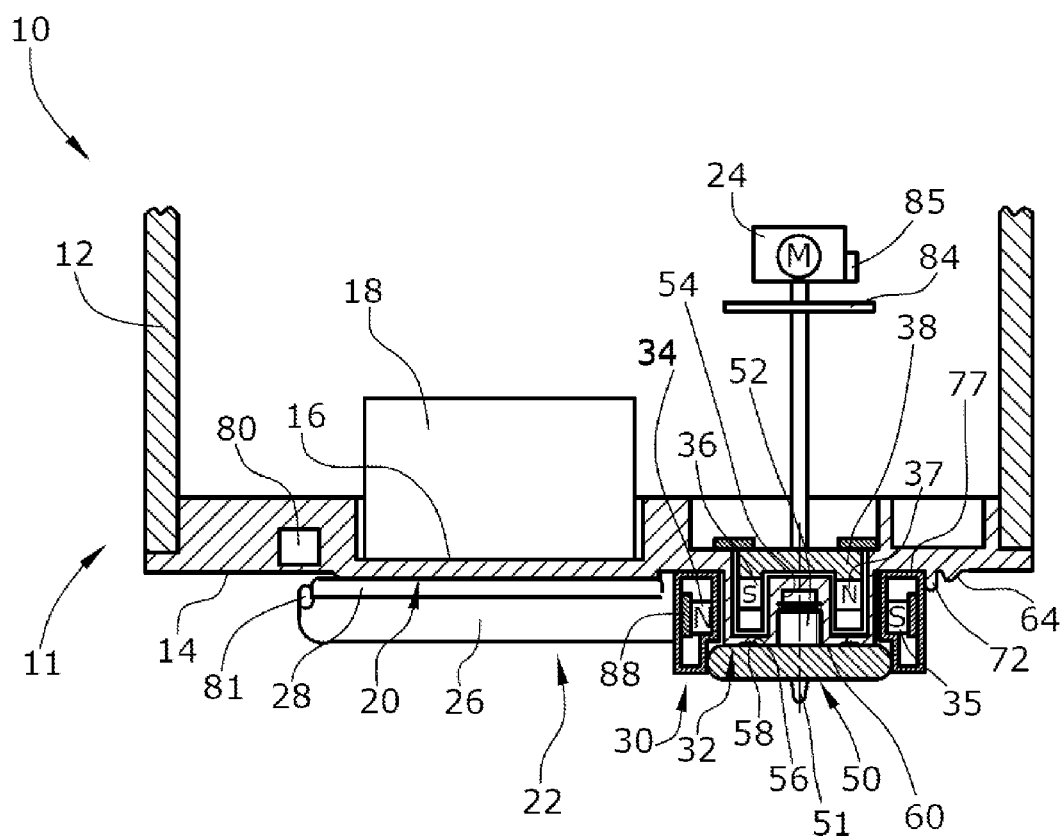
FIG. 2 is a cross sectional view of the waste water immersion probe of FIG. 1.

FIGS. 1 and 2 illustrate a waste water immersion probe 10 which, in the present case, is designed as an ultrasonic sludge blanket probe. The immersion probe 10 has a bipartite housing 11 formed by a pot-like housing body 12 and a circular disc-shaped housing cover 14 that forms the bottom housing wall of the housing 11. The housing body 12 is made of metal, whereas the housing cover 14 is made of plastic material. The housing body 12 and the housing cover 14 are fluid-tightly connected, e.g. screwed, glued or locked to each other. The waste water immersion probe 10 is intended for operation under permanent immersion in waste water.

On the inner side of the housing cover 14, a sensor 18 is arranged in a recess 16, which is designed as an ultrasonic sensor. The bottom of the recess 16 forms a sensor window 20 thin enough for the ultrasonic waves emitted and received by the ultrasonic sensor 18 to pass through in both directions substantially unimpeded.

The ultrasonic sensor 18 is rather sensitive to solid matter accreting on the outer side of the sensor window 20. For this reason, a pivotable wiper 22 is provided that regularly cleans the outer side of the sensor window 20 with oscillatory wiping movements. The wiper 22 is coupled with an electric drive motor 24 not through a shaft, but through a magnetic coupling, the electric motor being accommodated in the housing 11.

The wiper 22 basically consists of a wiper arm 26 with a wiper blade 28 and an annular body 30 of the wiper sitting on a pot 32 and enclosing the same. The pot 32 is formed integrally with the housing cover 14 and projects distally and axially from the same in a downward direction. Both the pot 32 and the annular body 30 are substantially cylindrical in shape. The housing cover 14 is designed devoid of openings.

The magnetic coupling of the wiper 22 with a stationary drive motor 24 is effected through permanent magnet elements 34, 35, 36, 37 that are fixedly secured in the annular body 30 or are arranged on a rotatably supported revolving ring 38 in the pot 32.

The revolving ring 38 is moved in an oscillating manner by the electric drive motor 24 which is stationarily mounted in the housing and is directly and co-axially connected with the revolving ring 38 through its drive motor shaft. The drive motor 24 performs an oscillatory pivoting movement via the drive shaft. As an alternative, the revolving ring may also be driven in an oscillating manner via an eccentric cam driven by a drive motor.

Basically, the immersion probe may also be configured as an optical probe for detecting the sludge blanket level, the turbidity or the nitrate content. In principle, the waste water immersion probe can determine parameters of the waste water which are determined through a sensor window that has to be kept clear of solid matter and soiling of all kind for the sensor to function precisely.

In general, a single permanent magnet element on the side of the wiper and on the side of the drive motor is sufficient. For a good guiding, however, at least two permanent magnet elements 34, 35, 36, 37 should be provided on either side so as to realize a rather uniform radial force distribution over the entire circumference. A multiple of two is technically reasonable as the number of magnetic elements. The permanent magnet elements 34, 35 associated with the wiper 22 are of a polarity opposite, with respect to the radial lines, to that of the respective radially opposite permanent magnet elements 36, 37 coupled with the drive motor 24. They are arranged in a ring shape, respectively, and may be realized with alternating polarities along the circumference. The magnetic elements 34, 35 of the wiper 22 are connected on the outside by means of a ferromagnetic closed yoke ring 88 that bundles and directs the magnetic flow.

The annular wiper body 30 is radially guided by a circular disc-shaped locking disc 50 screwed into a threaded bore 54 of the pot 32 by means of a central axial threaded bolt 52. The locking disc 50 has locking cams 56 on its proximal side that are locked in corresponding locking recesses 58 on the annular disc-shaped front face 60 of the pot 32. The locking disc 50 has a handle web 51 so that the locking disc 50 can be unlocked or locked manually by overcoming the locking forces.

An annular spoiler 64 is provided radially outside of the annular body 30, the spoiler being formed as a circumferential rib that projects axially from the housing cover 14 and radially covers a circular gap opening between the annular wiper body 30 and the housing cover 14. In particular, the spoiler 64 deflects fibrous solid matter from the gap opening so that their intrusion into the gap opening and a jamming of the annular wiper body 30 is avoided.

The oscillating movement of the wiper 22 is mechanically limited by two wiper-side stop noses 70, 71 and a cover-side stop web 72.

The annular wiper body 30 is spaced from the pot 32 and the locking disc 50, respectively, with a small radial and axial play, respectively. The radial guiding of the annular wiper body 30 is provided exclusively by the locking disc 50 along a linear and circular contact line, since the outer edge of the locking disc 50 is correspondingly convex. This results in a small contact area and rather small friction forces and moments that have to be overcome by the magnetic coupling.

The permanent magnet elements 34, 35 of the annular wiper body 30 on the one hand and the permanent magnet elements 36, 37 of the revolving ring 38 on the other hand are arranged offset in the axial direction by at least a few millimeters. The permanent magnet elements 34, 35 of the annular wiper body 30 are arranged more distally in the axial direction than the permanent magnet elements 36, 37 of the revolving ring 38. Thus, an axial bias of the annular wiper body 30 in the proximal direction is caused by which the proximal annular step surface 77 of the annular wiper body 30 is pressed on an annular surface of the housing cover 14. With rather little friction, the magnetic axial bias allows for an axial support of the annular wiper body 30 to be realized which, however, does still allow for small tilting movements of the wiper arm 26 should the same meet an obstacle.

For position detection purposes, the drive motor shaft is mounted with a decoder disc 84 read by an optical sensor 85. With this arrangement, the rotational position or the end position of the drive motor shaft or the wiper 22 can be detected. Alternatively or complementarily, for position detection purposes, the wiper arm 26 may have a permanent magnet 81 at its distal end and the housing cover 14 may have a Hall element 80 at a wiper end position or another defined position of the wiper 22. This creates a reference point that is passed in every wiping cycle by the wiper itself and allows, at any time, an exact adjustment of the wiped range swept by the wiper 22.

The invention claimed is:

1. A waste water immersion probe comprising a housing configured so as to be liquid-tight, the housing having a sensor disposed therein and a sensor window, wherein
the sensor window is associated with a wiper on an outer side, for cleaning the sensor window, and
the wiper is driven by a drive motor arranged in the housing,
characterized in that
the housing is devoid of openings,
the drive motor drives a magnetic drive motor element in the housing, and
the wiper is associated with a magnetic wiper element outside the housing such that the magnetic drive motor element generates a magnetic field permeating the housing and transmits a drive torque to the magnetic wiper element without a shaft.

2. The waste water immersion probe of claim 1, characterized in that the drive motor element and the magnetic wiper element are passive magnetic elements.

3. The waste water immersion probe of claim 1, characterized in that the magnetic drive motor element is an active magnetic element and the magnetic wiper element is a passive magnetic element.

4. The waste water immersion probe of claim 1, wherein the wiper is mobile in an oscillating wiping movement, and
wherein the housing further comprises a housing stop element and the wiper comprises a wiper stop element operable to limit the oscillating wiping movement of the wiper.

5. The waste water immersion probe of claim 4, wherein:
the wiper comprises an annular wiper body that is closed, wherein the annular wiper body contains the magnetic wiper element, and wherein the annular wiper body surrounds a pot containing the magnetic drive motor element;
a radial play is provided between the annular wiper body and the pot, wherein radial guiding is effected exclusively by a locking disc mounted centrally in an axial direction on the pot; and
the annular wiper body is biased axially by the magnetic wiper element and the magnetic drive motor element.

6. The waste water immersion probe of claim 4, wherein:
the wiper comprises an annular wiper body (30), and wherein the housing is associated with a spoiler radially covering a gap opening between the annular wiper body (and the housing;

a radial play is provided between the annular wiper body and a pot, wherein radial guiding is effected exclusively by a locking disc mounted centrally in an axial direction on the pot; and
the annular wiper body is biased axially by the magnetic wiper element and the magnetic drive motor element.

7. The waste water immersion probe of claim 4, wherein:
the wiper comprises an annular wiper body that is closed, wherein the annular wiper body contains the magnetic wiper element, and wherein the annular wiper body surrounds a pot containing the magnetic drive motor element;
a radial play is provided between the annular wiper body and the pot, wherein radial guiding is effected exclusively by a locking disc mounted centrally in an axial direction on the pot; and
the locking disc and the pot have locking elements by which the locking disc is operable to be locked to the pot in a locked position.

8. The waste water immersion probe of claim 4, wherein:
the wiper comprises an annular wiper body, and wherein the housing is associated with a spoiler radially covering a gap opening between the annular wiper body and the housing;
a radial play is provided between the annular wiper body and a pot, wherein radial guiding is effected exclusively by a locking disc mounted centrally in an axial direction on the pot; and
the locking disc and the pot have locking elements by which the locking disc is operable to be locked to the pot in a locked position.

9. The waste water immersion probe of claim 1, characterized in that the wiper comprises a closed annular wiper body, wherein the annular wiper body contains the magnetic wiper elements, and wherein the annular wiper body surrounds a pot containing the magnetic drive motor element.

10. The waste water immersion probe of claim 9, characterized in that a radial play is provided between the annular wiper body and the pot, wherein radial guiding is effected exclusively by a locking disc mounted centrally in an axial direction on the pot.

11. The waste water immersion probe of claim 10, characterized in that the locking disc and the pot have locking elements by which the locking disc is operable to be locked to the pot in a locked position.

12. The waste water immersion probe of claim 1, wherein the wiper comprises an annular wiper body, and wherein the housing is associated with a spoiler radially covering a gap opening between the annular wiper body and the housing.

13. The waste water immersion probe of claim 12, characterized in that a radial play is provided between the annular wiper body and a pot, wherein radial guiding is effected exclusively by a locking disc mounted centrally in an axial direction on the pot.

14. The waste water immersion probe of claim 13, wherein the annular wiper body is biased axially by the magnetic wiper element and the magnetic drive motor element.

15. The waste water immersion probe of claim 13, characterized in that the locking disc and the pot have locking elements by which the locking disc is operable to be locked to the pot in a locked position.

16. The waste water immersion probe of claim 1, further comprising an annular wiper body that is biased axially by the magnetic wiper element and the magnetic drive motor element.

\* \* \* \* \*